United States Patent [19]

Welsh

[11] Patent Number: 4,526,490

[45] Date of Patent: Jul. 2, 1985

[54] DISPENSER FOR FLOWABLE MATERIAL

[75] Inventor: Richard E. Welsh, Milford, Del.

[73] Assignee: Dentsply Research & Development Corp., Milford, Del.

[21] Appl. No.: 527,447

[22] Filed: Aug. 29, 1983

[51] Int. Cl.³ ............................................. B43M 11/06
[52] U.S. Cl. ......................................... 401/183; 401/6
[58] Field of Search ............... 401/183, 184, 185, 186, 401/261, 262, 263, 265, 137, 138, 139, 6

[56] References Cited

U.S. PATENT DOCUMENTS

| | | | |
|---|---|---|---|
| 2,049,973 | 8/1936 | Nesmith | 401/261 |
| 2,104,651 | 1/1938 | Hoffman, Jr. | |
| 2,219,604 | 10/1940 | Trotter | |
| 2,687,727 | 8/1954 | Lawshe | |
| 2,734,665 | 2/1956 | Flamm | |
| 3,088,470 | 10/1960 | Hall | 401/261 |
| 3,133,310 | 5/1964 | Yorker et al. | 401/262 |
| 3,879,141 | 4/1975 | Shulman | 401/183 X |
| 4,080,078 | 3/1978 | Halm | 401/262 |
| 4,274,555 | 1/1981 | Sneider | |

Primary Examiner—Hugh R. Chamblee
Assistant Examiner—Carolyn A. Harrison
Attorney, Agent, or Firm—C. Hercus Just; Edward J. Hanson, Jr.

[57] ABSTRACT

A dispenser for flowable material having a squeezable container formed with filling and discharge openings at opposite ends, a combination handle and closure member connectable to the filling opening, and a flexible discharge spout and second closure member being connectable selectively to the discharge opening of said container, the connections all having snap-acting co-engaging members and the discharge spout being elongated and flexible and of uniform very small diameter to control discharge of precise amounts of material directed to desired locations of use by an operator holding the dispenser pen-like in one hand.

4 Claims, 3 Drawing Figures

DISPENSER FOR FLOWABLE MATERIAL

BACKGROUND OF THE INVENTION

This invention pertains to a dispenser for liquid and/or otherwise flowable material. More particularly, the material with which the invention is adapted especially to contain and dispense is of a medical or quasi-medical nature including dental material, but not restricted thereto. In dispensing many types of liquid or flowable material, the particular use which the material is to be applied frequently controls the design of a dispenser to be used therewith so as, for example, to direct the material to a desired location, which not infrequently, may be of a small area or otherwise in a location difficult to reach, and, accordingly, the dispenser must be designed to achieve the desired result. While many types of syringes of medical or other nature have been developed heretofore, many of them have been operated by plungers which are manually actuated either solely by pushing the plunger manually or moving the plunger manually by means of screw threads or otherwise. Many types of such syringes and/or dispensers are well known. However, another type of dispenser which is well known comprises one in which the material is contained in a flexible compartment of a desired nature, the sides of the compartment being adapted to be squeezed toward each other to effect discharge of the material through a suitable nozzle. The present invention, to a certain extent, is directed to said class of dispensers but includes details of advantages not hereto known in the art. Examples of known dispensers of the above type are illustrated in the following patents: U.S. Pat. Nos.

2,104,651—Hoffman, Jr. Jan. 4, 1938
2,219,604—Trotter Oct. 29, 1940
2,687,727—Lawshe Aug. 31, 1954
2,734,665—Flamm Feb. 14, 1956
4,274,555—Sneider Jan. 23, 1981

As indicated above, the structures illustrated in the foregoing patents, in the main, are for specific purposes primarily different from the present invention, but nevertheless illustrating the basic principle of effective discharge by means of squeezing opposite sides of a collapsible container toward each other.

SUMMARY OF THE INVENTION

It is the principal object of the present invention to provide a dispenser having a container or compartment of predetermined size which is initially filled or substantially filled with a flowable material of a nature to be dispensed from a directed nozzle to a specific location of application of the material and, while not restricted thereto, such application is of a medical and/or dental nature such as by applying the material to a crevice or fissure in a tooth to seal the same. It is to be understood, however, that such purpose is not to be considered restricted, but merely illustrative. More importantly, the design of the dispenser is such that it enables the same to be held manually by the user in the same manner that a pen or pencil is held so as to contribute to accurate directing of the dispensed material to a desired location.

Another object of the invention is to form particularly the container or compartment of the dispenser from suitable material of limited flexibility so as to enable opposite side walls thereof to be squeezed towards each other sufficiently to effect a discharge of a desired quantity from the nozzle of the dispenser, one end of the container having a filling opening and the opposite end having a discharge opening, the filling end of the container also being arranged to have a plug-like closure connected thereto and an elongated stem or handle being affixed to the plug-like closure and extending therefrom, preferably in co-axial relationship to the axis of the container, the length of the stem or handle being adequate to extend at least into the connection between the thumb and forefinger of the user in the same manner in which a pen or pencil is held.

A further object of the invention is to provide the discharge end of the container with means to connect it preferably to a tubular discharge spout and this spout preferably being of a flexible nature and capable of being bent into a desired configuration to facilitate the discharge of material to a desired location with accuracy, the spout also being interchangeable with a second closure member by which the material within the container may be secured against discharge as when the same is being stored awaiting sale or within a dental operatory awaiting the next use thereof.

Still another object of the invention is to provide interfitting means between the plug-like closure and handle member and the filling end of the container with snap-acting co-engageable elements in order that when the container has been filled with a desired material, such as when the closure for the discharge end has been connected thereto, the plug-like member and handle thereon may be connected to the filling end of the container more or less for permanent connection if desired, in view of the fact, that when all of the material has been discharged from the container, the same may be discarded, particularly in view of the relatively inexpensive cost of the same notwithstanding the fact that the container may be refilled if desired.

One further object of the invention is to provide the discharge end of the container with a port member having an axial opening therethrough and to which the discharge spour and closure member therefor interchangeably and selectably may be attached, preferably by snap-acting co-engageable elements.

A still further object of the invention is to arrange the closure members respectively for the filling and discharge ends of the container, as well as the discharge spout for the discharge end of the container, with telescopically interengageable mean which effect tight connections thereof and, for all practical purposes, leak-proof connections, by means of employing interfitting circular grooves and complimentary annular projections, which are rounded in cross-section, and thereby effect snap-acting securements for the assembled objects.

Details of the foregoing objects and of the invention, as well as other objects thereof, are set forth in the following specification and illustrated in the accompanying drawings comprising a part thereof.

DETAILS OF THE PREFERRED EMBODIMENT OF THE INVENTION

Figure 1:
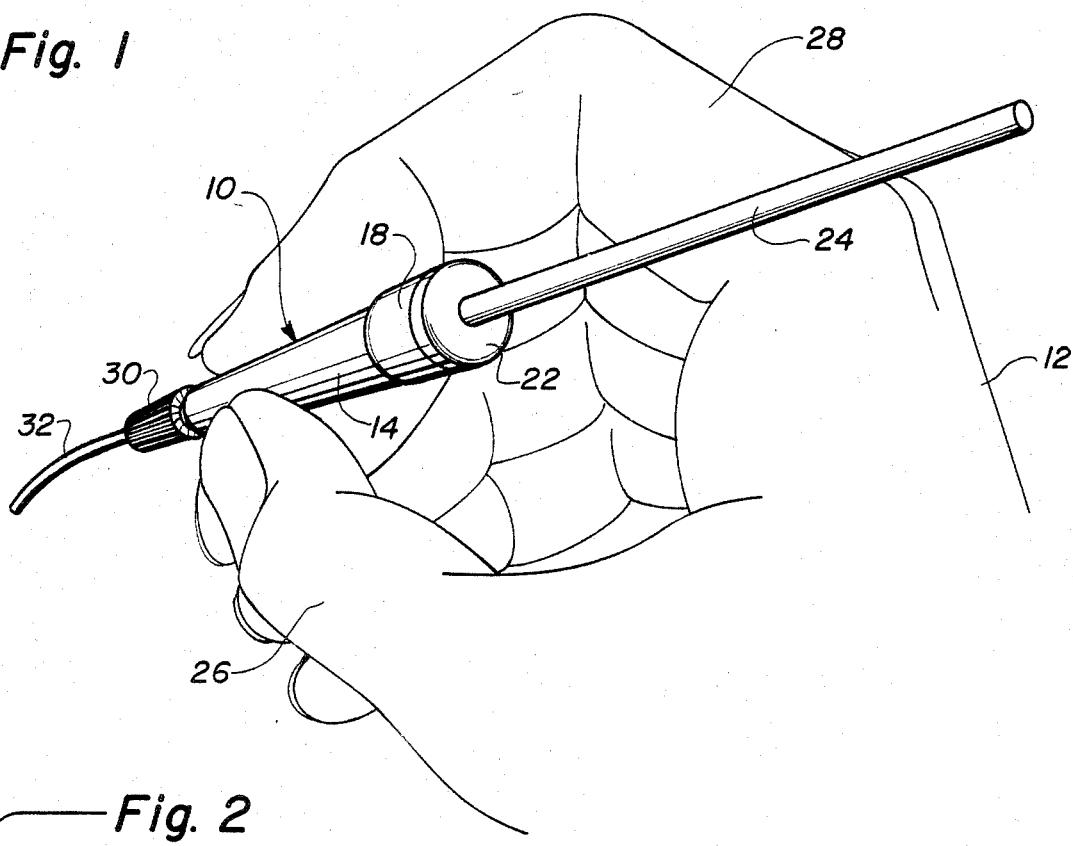
FIG. 1 is a perspective view of a dispenser embodying the present invention and illustrated as being held like a pen or a pencil in a human hand.
Figure 3:
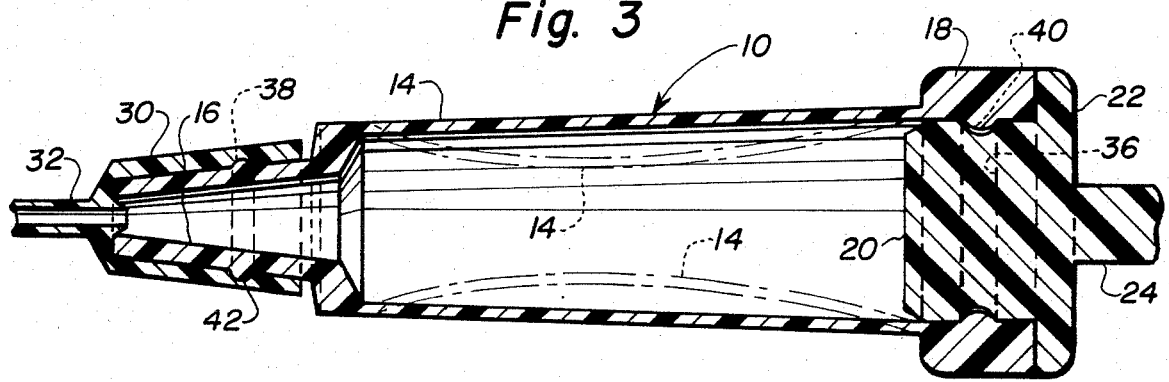
FIG. 3 is an elongated sectional view, partly fragmentated at opposite ends thereof, and showing on a larger scale than in the preceding figure the details of the manner in which the various elements in FIG. 2 are assembled in operative position as otherwise illustrated in FIG. 1.

Referring to FIG. 1, there is illustrated therein a dispenser 10 which is shown in a human hand 12 and illustrating the preferred manner in which the dispenser is to be used in accordance with the invention. It will be seen that the dispenser comprises a compartment or container 14 which preferably is substantially circular in cross-section and the walls thereof, as seen in FIG. 3, are of limited uniform thickness. The material from which the container is formed preferably is a suitable plastic material of at least limited flexibility, such as polyethylene of suitable consistency, whereby the opposite walls may be manually compressed toward each other, as shown in phantom in FIG. 3, adequately to effect discharge of a desired amount of material therefrom through discharge opening 16, at a desired rate, at one end of the container 14.

Figure 2:
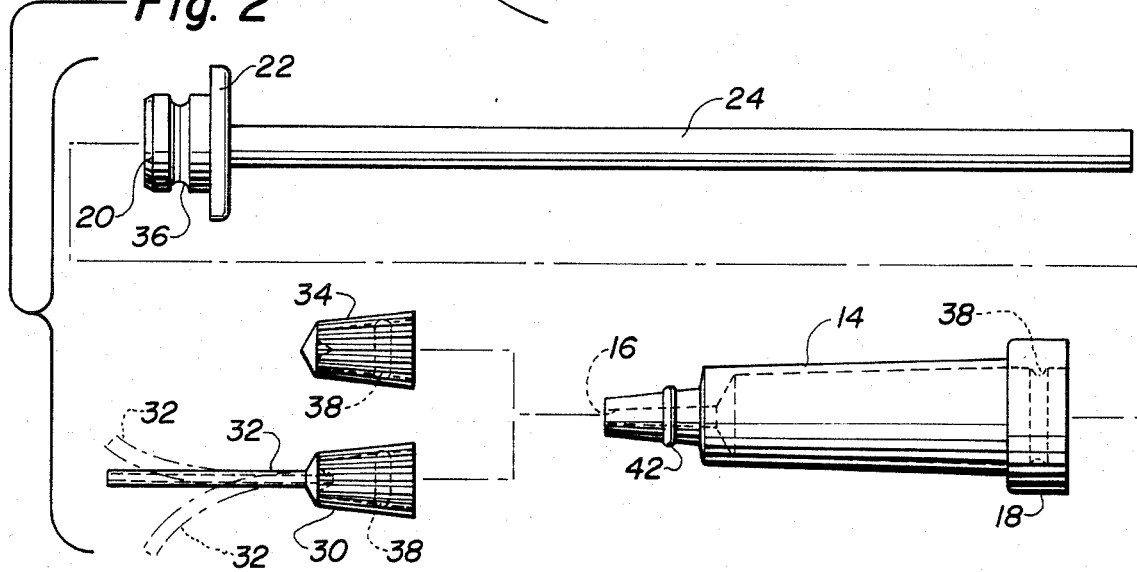
FIG. 2 is a foreshortened exploded view illustrating the various elements which are connected together in the dispenser shown in FIG. 1, the arrangement of the elements being indicated by a phantom guideline and several alternative curved positions of the discharge spout being shown in phantom.

It will be seen that the discharge opening 16 is somewhat in the nature of a port member and preferably is frusto-conical in shape as clearly shown in FIG. 2. The opposite end of the container 14 is provided with an enlarged collar 18 having an opening therethrough comprising a filling opening, into which a first closure member 20 is inserted tightly, the same being plug-like and provided with a flange 22 of a diameter similar to that of the collar 18 and adapted to abut the outer end of said collar tightly. Closure member 20 also is a combined closure and handle 24, the handle preferably being molded integrally with the closure member 20 and said combination member may be molded from the same material as that from which the container 14 is formed.

From FIG. 1, it will be seen that the handle 24 is of sufficient length that it may be disposed or positioned within the space between the users thumb 26 and forefinger 28, somewhat in the manner in which a pen or pencil is held in the human hand, such arrangement being for purpose of facilitating the directing of the discharge from the dispenser to a desired location and otherwise facilitate the holding of the container 14 functionally between the thumb and forefinger of the user.

The discharge member 16, which has a discharge opening therethrough, also selectively is adapted to be disposed within a thimble-like spout member 30 having a socket complementary to the outer surface of discharge member 16 and terminating at the outer end thereof in a flexible nozzle or spout 32, which extends from the spout member 30 a limited distance, and preferably is of uniform diameter. It preferably is formed from the same material, for example, as that from which the container 14 is formed. Also, by way of example but without limitation thereto, especially if the material to be dispensed is of a relatively fluid nature, it has been found that the opening in the nozzle 32 may be of approximately 0.030 inches and the outside diameter is 0.050 inches, whereby when the side walls of the container 14 are squeezed a limited distance toward each other, a desired amount of material may be dispensed from the nozzle accurately to a desired location with substantial preciseness. Upon releasing the sides of container 14, flow is instantly stopped and actually may even be retracted into the nozzle of discharge member 16. Further, the material from which the flexible nozzle 32 is formed is such that the same may be bent to a desired extent in order to facilitate the discharge of material precisely to a desired location. Further, the exterior of the thimble-like spout member 30 may be serrated, if desired, to facilitate the application thereof to the discharge member 16.

When the material is to be stored within the container 14, such as while the dispenser is awaiting sale or after a discharge of material therefrom, the spout member 30 may be removed therefrom and replaced by a thimble-like cap 34, shown in FIG. 2, which may have the same interior shape as that of the spout member 30 for close conformity to the exterior of the discharge member 16.

To facilitate securing selectively either the spout member 30 or cap 34 to the discharge member 16, as well as for firmly connecting the first closure member 20 within the filling opening within the enlarged collar 18, the invention includes snap-acting co-engageable members in the form of a circular groove 36 (see FIG. 2) in the plug-like closure member 20 and similar circular groove 38 in the spout member 30 and cap 34 which are complementary to annular projection 40 within the filling opening in collar 18 and annular projection 42 exteriorly of the discharge member 16. In cross section, the annular projections 40 and 42 are rounded and are closely complimentary to the grooves 36 and 38, thereby affording tight connection of the spout member or cap to the discharge member 16 and the plug-like closure member 20 to the filling opening of the container 14. Also, it will be seen that the engagements of said aforementioned elements respectively with the opposite ends of the container 14 are of a telescopic nature and, as indicated above, for practical purposes, when plug-like closure member 20 and handle 24 are connected to the filling opening of the container 14, such connection may be considered to be of a fixed nature. In normal use, the container is discarded, but such container may be refilled if desired by removing the plug-like closure member 20 from the filling end thereof.

From the foregoing, it will be seen that the present invention provides a highly useful dispenser for flowable material either of a relatively fluid nature or even of a somewhat viscous nature. Obviously, the diameter of the flexible nozzle 32 will be determined in relation particularly to the nature of the material to be dispensed therethrough. Attachment and removal respectively and selectively of the spout member 30 and cap 34 relative to discharge member 16 is readily effected. Also, the capacity of container 14 is determined in relation to the type and nature of the material to be stored therein or dispensed therefrom and the dispenser, even when filled, is of very light weight and is readily handled and manipulated in the manner described above.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown therein.

It is claimed:

1. A dispenser adapted for manual manipulation comprising in combination, a container which is circular in cross-section having flexible walls adapted to be squeezed toward each other to effect discharge of material and having a filling opening at one end and a discharge opening at the opposite end, a flanged plug-like first closure member having an elongated handle member of substantially smaller diameter than said container extending axially from one end of said container and having a length approximately twice that of said container, said first closure member being separably connected tightly to the filling opening of said container and said handle being adapted to facilitate manually holding the container between the thumb and forefinger of a user similarly to the manner of holding a pen when writing to guide the dispenser when effecting discharge of contents of said container at desired locations, the discharge opening being adapted to be connected selectively to a second closure member and a tubular discharge spout, and the filling end of said container having an enlarged collar to facilitate effecting a leakproof connection of said filling end with said flanged first closure member.

2. The dispenser according to claim 1 further characterized by said plug and filling opening having snap-acting means operable to secure the connection of the plug and container and also sealing the contents of said container, and said plug having a flange abutting the outer end of the filling opening of said container to facilitate positioning the plug in said opening.

3. The dispenser according to claim 1 further characterized by said discharge opening being a longitudinal port member and said tubular discharge spout having a cup-shaped portion complementary to and tightly receiving said port member, and said port member and discharge spout respectively having a co-engaging snap-acting connecting means.

4. The dispenser according to claim 3 further characterized by said tubular discharge spout being flexible and of uniform diameter which is very substantially smaller than that of said container and suitable to regulate a precise quantity of discharge of material to desired locations.

* * * * *